United States Patent
Copmans et al.

(10) Patent No.: US 11,180,480 B2
(45) Date of Patent: Nov. 23, 2021

(54) SYNTHESIS OF 4-AMINOPYRIMIDINE COMPOUNDS

(71) Applicant: SENSORION, Montpellier (FR)

(72) Inventors: Daan Copmans, Lille (BE); Amandine Mohr, DA Weert (NL); Maurice Hubert Bonten, SH Heerlen (NL); Dawn Toronto, Bend, OR (US)

(73) Assignee: SENSORION, Montpellier (FR)

( * ) Notice: Subject to any disclaimer, the term of this patent is extended or adjusted under 35 U.S.C. 154(b) by 0 days.

(21) Appl. No.: 16/757,008

(22) PCT Filed: Oct. 17, 2018

(86) PCT No.: PCT/EP2018/078385
§ 371 (c)(1),
(2) Date: Apr. 17, 2020

(87) PCT Pub. No.: WO2019/076974
PCT Pub. Date: Apr. 25, 2019

(65) Prior Publication Data
US 2020/0270228 A1    Aug. 27, 2020

(30) Foreign Application Priority Data
Oct. 17, 2017   (EP) .................... 17306404

(51) Int. Cl.
  *C07D 403/04*        (2006.01)
(52) U.S. Cl.
  CPC ................. *C07D 403/04* (2013.01)
(58) Field of Classification Search
  CPC ..... C07D 403/04; A61K 31/506; A61P 29/00; A61P 37/00
  See application file for complete search history.

(56) References Cited

U.S. PATENT DOCUMENTS

| 8,415,366 B2* | 4/2013 | Edwards ................ A61P 19/02 514/275 |
| 2010/0234354 A1 | 9/2010 | Dorsch et al. |
| 2010/0273796 A1 | 10/2010 | Dorsch et al. |
| 2011/0034474 A1 | 2/2011 | Dorsch et al. |
| 2011/0092498 A1 | 4/2011 | Dorsch et al. |
| 2011/0257180 A1 | 10/2011 | Becker et al. |
| 2011/0263596 A1 | 10/2011 | Schadt et al. |
| 2012/0245140 A1 | 9/2012 | Almansa Rosales et al. |
| 2012/0295908 A1 | 11/2012 | Schadt et al. |

FOREIGN PATENT DOCUMENTS

| WO | 2009080721 A2 | 7/2009 |
| WO | 2010072829 A1 | 7/2010 |
| WO | 2011076878 A1 | 6/2011 |
| WO | 2013182711 A1 | 12/2013 |

OTHER PUBLICATIONS

Robinson, Medical Therapy of Inflammatory Bowel Disease for the 21st Century, Eur J Suppl 582, pp. 90-98, 1998.*
Singh et al., Immune Therapy in inflammatory bowel disease and models of colitis, British Journal of Surgery, 88, pp. 1558-1569, 2001.*
Gantner et al., Histamine H4 and H2 Receptors Control Histamine-induced Interleukin-16 Release from Human CD8 T Cells, The Journal of Pharmacology and Experimental Therapeutics, vol. 303, No. 1, pp. 300-307 (2002).*
De Esch et al., The Histamine H4 receptor as a new therapeutic target for inflammation, Trends in Pharmacological Sciences, vol. 26, No. 9, pp. 462-468 (2005).*
International Search Report dated Nov. 13, 2018, in connection with corresponding International Application No. PCT/EP2018/078385; 4 pages.

* cited by examiner

*Primary Examiner* — Deepak R Rao
(74) *Attorney, Agent, or Firm* — Maier & Maier, PLLC

(57) ABSTRACT

A process for manufacturing 2-isobutyl-6-(3-(methylamino) azetidin-1-yl)pyrimidin-4-amine of Formula (I):

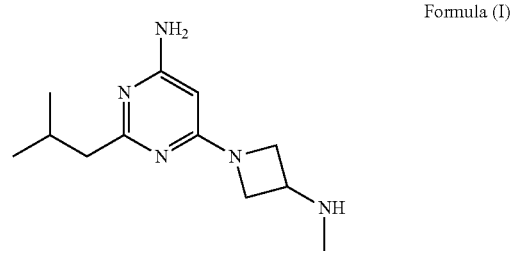

Formula (I)

including starting from 6-chloro-2-isobutylpyrimidin-4-amine and tert-butyl azetidin-3-yl(methyl)carbamate, or another N-protected N-methylazetidin-3-amine, and performing the following steps: (a) coupling reaction of both compounds in dimethylsulfoxide in presence of potassium carbonate to afford an intermediate protected compound; and (b) deprotection of the protected compound to afford 2-isobutyl-6-(3-(methylamino)azetidin-1-yl)pyrimidin-4-amine. Also, a process for manufacturing the intermediate protected compound, wherein deprotection step (b) is omitted, and the compounds obtained from the processes.

21 Claims, No Drawings

SYNTHESIS OF 4-AMINOPYRIMIDINE COMPOUNDS

FIELD

The present invention pertains to the field of the manufacture of organic compounds. The present invention especially relates to the synthesis of 2-isobutyl-6-(3-(methylamino)azetidin-1-yl)pyrimidin-4-amine.

BACKGROUND 4-aminopyrimidine derivatives are a class of compounds of general Formula (A):

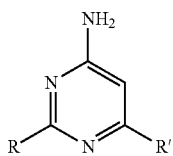

Formula (A)

which are useful as therapeutically active ingredients, especially as histamine H4 receptor antagonists.

Among 4-aminopyrimidine derivatives, 2-isobutyl-6-(3-(methylamino)azetidin-1-yl)pyrimidin-4-amine of Formula (I) (hereafter "Compound (I)", in short "(I)") is of particular interest:

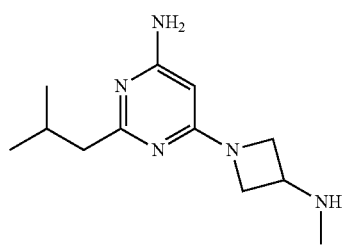

Formula (I)

WO 2009/080721 patent application describes the compound of Formula (I) and several different synthetic methods thereof, especially the base-assisted coupling of a chlorinated aromatic compound with a tert-Butyloxycarbonyl (Boc)-protected heterocyclic secondary diamine as represented on Scheme 1 below:

Scheme 1

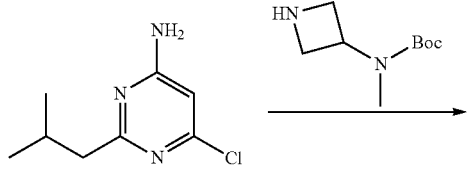

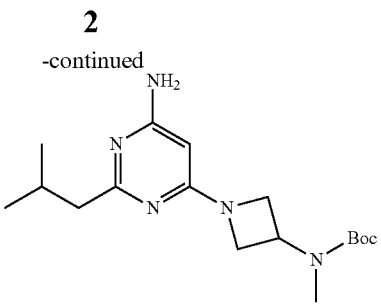

This reaction is carried out in presence of N, N-diisopropylethylamine (DIPEA) as base in refluxing ethanol (EtOH). Boc-protected intermediate compound is then submitted to a deprotection step in order to provide Compound (I). Deprotection step is made by means of hydrochloric acid (HCl) in methanol (MeOH) at room temperature, directly on intermediate compound which is not isolated beforehand.

WO 2009/080721 process has many drawbacks which significantly limit industrial synthesis of Compound (I). Especially, during coupling step:
- conversion is slow, so that prolonged reaction time (at least 2 days) is required in order to reach sufficient conversion of chlorinated aromatic compound in intermediate compound;
- conversion is incomplete, so that synthesized intermediate compound is mixed with unreacted chlorinated aromatic compound and/or unreacted heterocyclic secondary diamine; and
- the heterocyclic secondary diamine is degraded in reaction medium, so that its degradation products are present with synthetized intermediate compound, and so that high excess of heterocyclic secondary diamine has to be added portion wise to compensate the degradation of this compound.

All these factors concur to the high operation cost of prior art manufacturing processes, although they merely achieve low yield and poor purity of Compound (I). The insufficient purity requests extensive purification step by chromatography. Therefore, existing processes do not suit the needs of modern industry in terms of costs and environmental impact.

The Applicant realized in-depth research in order to improve the manufacturing method of Compound (I) and surprisingly found that selecting very specific experimental conditions overcome the limitations of prior art process, especially coupling step limitations.

SUMMARY

This invention relates to a process for manufacturing 2-isobutyl-6-(3-(methylamino)azetidin-1-yl)pyrimidin-4-amine of Formula (I), as described below, the process comprising the following steps:
 (a) reacting 6-chloro-2-isobutylpyrimidin-4-amine of Formula (III), as described below, with a N-protected N-methylazetidin-3-amine of Formula (IV), as described below,
  in an organic solvent being dimethylsulfoxide (DMSO);
  in the presence of a base being potassium carbonate ($K_2CO_3$);
  at a temperature ranging from 85 to 125° C.;
  the initial molar ratio between the compound of Formula (IV) and the compound of Formula (III) ranging from 0.85 to 1.25;

so as to obtain an intermediate protected compound of Formula (II), as described below;

and (b) performing a N-deprotection of the compound of Formula (II); so as to obtain the compound of Formula (I).

According to an embodiment, the protecting group is tert-Butyloxycarbonyl (Boc) or Tosyl (Ts), preferably Boc.

According to an embodiment, the initial molar ratio at coupling step (a) between the compound of Formula (IV) and the compound of Formula (III) ranges from 0.90 to 1.20, preferably from 0.95 to 1.10, more preferably from 0.99 to 1.09. In an embodiment, the initial molar ratio at coupling step (a) between the compound of Formula (IV) and the compound of Formula (III) is 1.04.

According to an embodiment, the temperature during coupling step (a) ranges from 90 to 120° C., preferably from 100 to 120° C., more preferably from 105 to 115° C. In an embodiment, the temperature during coupling step (a) is 110° C.

According to an embodiment, the reaction time of coupling step (a) ranges from 16 h to 32 h, preferably from 20 to 24 h.

According to an embodiment, coupling step (a) is followed by a workup and isolation step (a') comprising the following steps: (a'-1) dilution of reaction mixture with water and with a first polar aprotic organic solvent; (a'-2) phase separation, and optionally washing by water; (a'-3) solvent switch from the first solvent to a second polar aprotic organic solvent; (a'-4) recrystallisation by cooling; and (a'-5) filtration; to afford the compound of Formula (II). In an embodiment, the polar aprotic organic solvent at dilution step (a'-1) is ethyl acetate. In an embodiment, the polar aprotic organic solvent at solvent switch step (a'-3) is isopropyl acetate.

According to an embodiment, coupling step (a) or workup and isolation step (a') is followed by a purification step (a") comprising a step of recrystallisation of the compound of Formula (II) in a polar aprotic organic solvent, preferably isopropyl acetate.

According to an embodiment, deprotection step (b) is made by means of contacting the compound of Formula (II) with dilute aqueous hydrochloric acid solution, preferably 30% w/w aqueous hydrochloric acid solution.

According to an embodiment, the initial molar ratio between the compound of Formula (II) and hydrochloric acid ranges from 6 to 10, preferably from 7 to 9, more preferably is 7.9.

The invention also relates to a process for manufacturing a compound of Formula (II), as described below, the process comprising:

reacting 6-chloro-2-isobutylpyrimidin-4-amine of Formula (III), as described below, with a N-protected N-methylazetidin-3-amine of Formula (IV), as described below;

in an organic solvent being dimethylsulfoxide;

in the presence of a base being potassium carbonate;

at a temperature ranging from 85 to 125° C.;

the initial molar ratio between the compound of Formula (IV) and the compound of Formula (III) ranging from 0.85 to 1.25;

so as to obtain the compound of Formula (II).

The invention also relates to a compound of Formula (I):

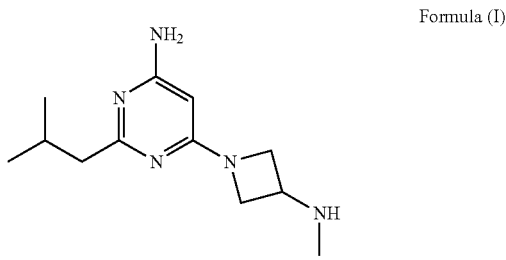 [SMILES: CNC1CN(c2cc(N)nc(CC(C)C)n2)C1]

Formula (I)

manufactured by a process according to the invention.

The invention also relates to a compound of Formula (II):

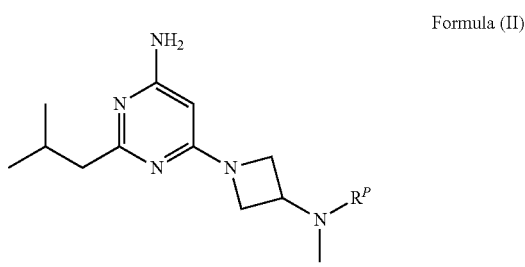

Formula (II)

wherein $R^P$ is a protecting group;

manufactured by a process according to the invention.

The present invention also relates to a compound of Formula (I) as described herein, for use in treating a disease mediated by the H4 histamine receptor.

DETAILED DESCRIPTION

In the present invention, the following terms have the following meanings:

"About" preceding a figure means plus or less 10% of the value of said figure.

"Molar ratio" refers the relative proportions of reactants that are used in a chemical reaction. Molar ratio between a reactant A and another reactant B is calculated by dividing the molar amount of reactant A by the molar amount of reactant B. Unless otherwise specified, moral ratio relates to initial moral ratio, i.e. to the moral ratio between introduced molar amounts of reactants, before any reaction thereof.

"Protecting group" refers to a suitable organic moiety used to protect a certain functional group in a chemical synthesis. In the present invention, protected functional group is secondary amine group (—NHRR') and protecting group refers to a secondary amine protecting group, preferably tert-butyloxycarbonyl (Boc).

"Solvate" is used herein to describe a molecular complex comprising the compound of Formula I of the invention and one or more pharmaceutically acceptable solvent molecules, for example, ethanol. The term "hydrate" is employed when said solvent is water.

By "pharmaceutically acceptable" is meant that the ingredients of a pharmaceutical composition are compatible with each other and not deleterious to the subject to which it is administered.

"Pharmaceutically acceptable excipient" refers to an excipient that does not produce any adverse, allergic or other unwanted reactions when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety, quality and purity standards as required by regulatory offices, such as, for example, FDA Office or EMA.

"Subject" refers to a mammal, preferably a human. In one embodiment, the subject is a pet, including, without limitation, a dog, a cat, a guinea pig, a hamster, a rat, a mouse, a ferret, a rabbit, a bird or an amphibian. In one embodiment, a subject may be a "patient", i.e., a female or a male, an adult or a child, who/which is awaiting the receipt of, or is receiving medical care or was/is/will be the object of a medical procedure, or is monitored for the development of a disease mediated by the H4 histamine receptor or of an ear disease, disorder or condition.

"Therapeutically effective amount" refers to level or amount of agent that is aimed at, without causing significant negative or adverse side effects to the target, (1) delaying or preventing the onset of the targeted pathologic condition or disorder; (2) slowing down or stopping the progression, aggravation, or deterioration of one or more symptoms of the targeted pathologic condition or disorder; (3) bringing about ameliorations of the symptoms of the targeted pathologic condition or disorder; (4) reducing the severity or incidence of the targeted pathologic condition or disorder; or (5) curing the targeted pathologic condition or disorder. A therapeutically effective amount may be administered prior to the onset of the targeted pathologic condition or disorder, for a prophylactic or preventive action. Alternatively or additionally, the therapeutically effective amount may be administered after onset of the targeted pathologic condition or disorder, for a therapeutic action. In one embodiment, a therapeutically effective amount of the composition is an amount that is effective in reducing at least one symptom of the targeted pathologic condition or disorder.

"Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for the targeted pathologic disorder if, after receiving a therapeutic amount of the compound or composition of the present invention, the subject or mammal shows observable effects on one or more of the followings: (i) relief to some extent of one or more of the symptoms associated with the specific disorder or condition (such as, for example, vertigo, dizziness and tinnitus in the case of an ear disease); (ii) reduced morbidity and mortality, and (iii) improvement in quality of life issues. In one embodiment, the targeted pathologic condition or disorder is an ear disorder, and the term "treated" may refer to promotion of ear functioning; or decrease in hearing loss. The above parameters for assessing successful treatment and improvement in the disorder are readily measurable by routine procedures familiar to a physician.

"Lesional vestibular disorders" refer to vestibular disorders wherein lesions of inner ear cells and/or vestibular nerve are present or will appear during the disorder time course. In this case, the functionality of the vestibule is impaired. However, morphofunctional alterations of the vestibular endorgans cannot be evaluated directly (except for large lesions that can be detected by MRI). Conversely, indirect assessment methods are currently used to evaluate the loss of functionality of the vestibule. These testing methods are generally conducted at ENT clinic/hospitals. Examples of such methods include, but are not limited to, the videonystagmography (VNG) and assessment of the vestibulo-ocular reflex (VOR) using caloric or rotational tests, video head impulse testing (vHIT) and vestibular evoked myogenic potentials (VEMP). Lesional vestibular disorders include, but are not limited to:

vestibular disorders wherein an inflammation of the inner ear and/or the vestibular nerve induces reversible and/or irreversible damages. Examples of conditions from this group include, but are not limited to, vestibular neuritis, acute unilateral vestibulopathy and vestibular neuronitis;

vestibular disorders wherein inner ear fluids are affected (abnormalities in the quantity, composition, and/or pressure of the endolymph), these disorders usually develop lesions during the disease time course. Examples of conditions from this group are Menière's disease and secondary endolymphatic hydrops. They are associated with tinnitus and hearing loss;

vestibular disorders induced by insults or lesions of the vestibular endorgans. Examples of said conditions are vertigo caused by local ischemia, excitotoxicity, trauma that affect temporal bones or ototoxic insult to vestibular hair cells by drugs such as gentamicin and cisplatin;

iterative vestibular disorders of unknown origin leading to permanent vestibular deficits, but without tinnitus or hearing loss. An example of a condition from this group is vestibular migraine (or migrainous vertigo).

"Non-lesional vestibular disorders" refer to vestibular disorders supported by transient and often iterative vertigo crisis wherein no lesion on inner ear cells and/or vestibular nerve can be observed. In this case, the functionality of the vestibule evaluated between the vertigo crisis using functional tests (VOR, VNG) does not differ from healthy vestibule. Non-lesional vestibular disorders include, but are not limited to:

vestibular disorders wherein debris had been collected within a part of the inner ear. This debris, called otoconia, is made up of small crystals of calcium carbonate and when they shift, they send false signals to the brain. Examples of said conditions include, but are not limited to, positional vertigos and in particular benign paroxysmal positional vertigo (BPPV);

iterative vestibular disorders of unknown origin without tinnitus, hearing loss or permanent vestibular deficits.

In the present invention, the following abbreviations have the following meanings:

2-MeTHF: 2-methyltetrahydrofurane;
ACN: acetonitrile;
AcOH: acetic acid;
AL: aqueous layer;
Boc: tert-butyloxycarbonyl;
DIPEA: N, N'-diisopropylethylamine;
DMSO: dimethylsulfoxide;

EtOAc: ethyl acetate;
EtOH: ethanol;
GC: gas chromatography;
HCl: hydrochloric acid;
HLPC: high-performance liquid chromatography;
H$_2$O: water;
iPAc: isopropyl acetate;
MeOH: methanol;
MTBE: methyl tert-butyl ether;
NaOEt: sodium ethoxide;
NH$_3$: ammonia;
OL: oil layer;
POCl$_3$: phosphoryl chloride;
RT: room temperature.

This invention relates to a novel process for manufacturing 2-isobutyl-6-(3-(methylamino)azetidin-1-yl)pyrimidin-4-amine ("Compound (I)", in short "(I)") of Formula (I):

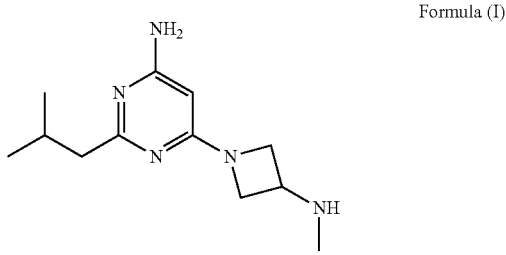 [SMILES: CNC1CN(c2cc(N)nc(CC(C)C)n2)C1]

Formula (I)

the process comprising the following steps:
(a) reacting 6-chloro-2-isobutylpyrimidin-4-amine ("Compound (III)", in short "(III)") of Formula (III):

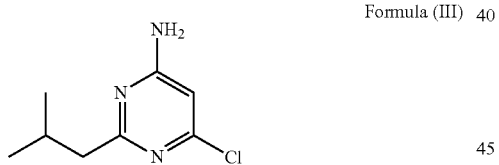

Formula (III)

with a N-protected N-methylazetidin-3-amine (hereafter "Compound (IV)", in short "(IV)") of Formula (IV):

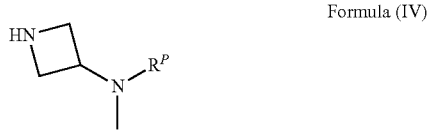

Formula (IV)

wherein R$^P$ is a protecting group;
in dimethylsulfoxide (DMSO) as organic solvent;
in the presence of potassium carbonate (K$_2$CO$_3$) as base;
at a temperature ranging from 85 to 125° C.;
the initial molar ratio between Compound (IV) and Compound (III) ranging from 0.85 to 1.25;
so as to obtain an intermediate protected compound ("Compound (II)", in short "(II)") of Formula (II):

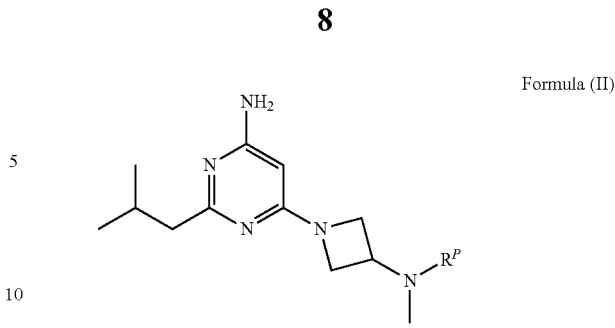

Formula (II)

wherein R$^P$ is a protecting group;
and
(b) performing a deprotection of Compound (II);
so as to obtain Compound (I).

This process according to the invention is represented in Scheme 2 below:

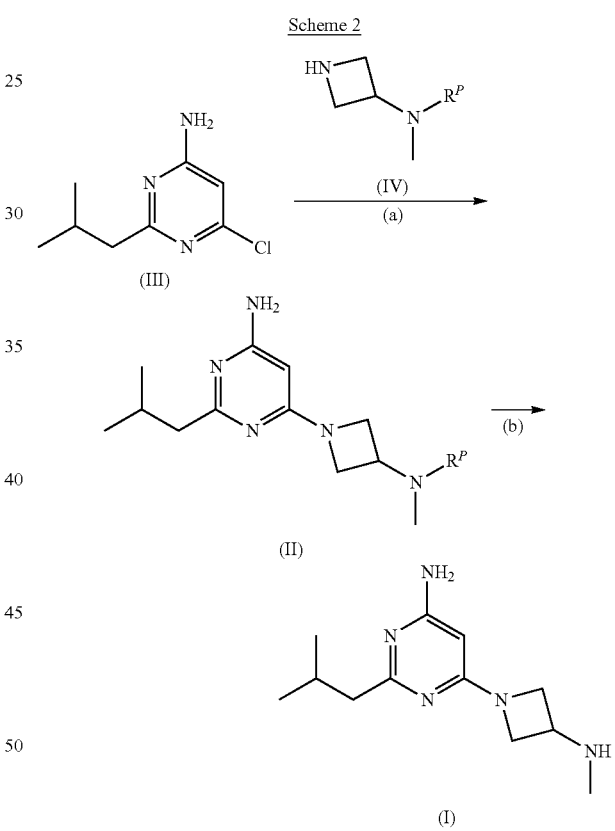

Scheme 2

According to an embodiment, protecting group R$^P$ is an organic moiety selected from Carbobenzyloxy (CBz), p-Methoxybenzyl carbonyl (Moz), tert-Butyloxycarbonyl (Boc), 9-Fluorenylmethyloxycarbonyl (FMOC), Acetyl (Ac), Benzoyl (Bz), Benzyl (Bn), Carbamate, p-Methoxybenzyl (PMB), 3,4-Dimethoxybenzyl (DMPM), p-Methoxyphenyl (PMP), Tosyl (Ts), and Trichloroethyl chloroformate (Troc). In an embodiment, protecting group R$^P$ is Ts or Boc. In a preferred embodiment, protecting group R$^P$ is tert-butyloxycarbonyl (Boc). In this preferred embodiment, Compound (IV) is tert-butyl azetidin-3-yl(methyl)carbamate of Formula (IV'):

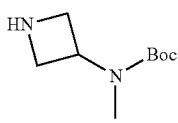

Formula (IV')

and Compound (II) is tert-butyl (1-(6-amino-2-isobutylpyrimidin-4-yl)azetidin-3-yl)(methyl)carbamate of Formula (II'):

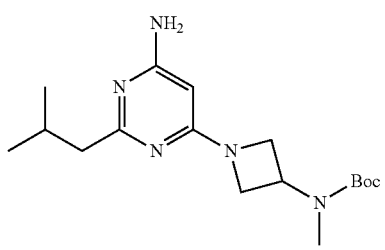

Formula (II')

According to an embodiment, the initial molar ratio at coupling step (a) between Compound (IV) and Compound (III) ranges from 0.90 to 1.20, preferably from 0.95 to 1.10, more preferably from 0.99 to 1.09, more preferably is 1.04.

According to an embodiment, the initial molar ratio at coupling step (a) between $K_2CO_3$ and Compound (III) ranges from 1.05 to 1.5, preferably from 1.1 to 1.3, more preferably from 1.15 to 1.25, more preferably is 1.2.

According to an embodiment, the temperature during coupling step (a) ranges from 90 to 120° C., preferably from 100 to 120° C., more preferably from 105 to 115° C., more preferably is 110° C.

According to an embodiment, the reaction time of coupling step (a) is at least 12 h, preferably at least 16 h, more preferably at least 20 h. In an embodiment, the reaction time of coupling step (a) is not higher than 48 h, preferably not higher than 32 h, more preferably not higher than 24 h. In a preferred embodiment, the reaction time ranges from 20 to 24 h.

Advantageously, conversion of Compounds (III) and (IV) in Compound (II) after coupling step (a) is at least 90%, preferably at least 95%, more preferably at least 98%.

According to an embodiment, coupling step (a) is followed by a work-up and isolation step (a') comprising the following sub-steps:
(a'-1) dilution of reaction mixture with water and with a first polar aprotic organic solvent, preferably ethyl acetate (EtOAc);
(a'-2) phase separation, and optionally washing by water;
(a'-3) solvent switch from the first solvent to a second polar aprotic organic solvent, preferably isopropyl acetate (iPAc);
(a'-4) recrystallisation by cooling; and
(a'-5) filtration;
so as to obtain isolated Compound (II).

Following work-up and isolation step (a'), Compound (II) is isolated as a solid. Advantageously, Compound (II) is obtained after workup and isolation step (a') with at least 80% yield, preferably at least 85% yield, more preferably at least 90% yield.

According to an embodiment, coupling step (a) or work-up and isolation step (a') is followed by a purification step (a") comprising a step of recrystallisation of Compound (II) in a polar aprotic organic solvent, preferably isopropyl acetate (iPAc); so as to obtain purified Compound (II). Advantageously, Compound (II) is obtained after purification step (a") with at least 75% yield, preferably at least 80% yield, more preferably at least 85% yield. Advantageously, Compound (II) is obtained after purification step (a") with at least 95% purity, preferably at least 99% purity, more preferably at least 99.5% purity. Especially, Compound (II) is advantageously obtained after purification step (a") with less than 100 ppm of Compound (IV).

According to an embodiment, deprotection step (b) is made through acidification, preferably by means of contacting Compound (II) with dilute hydrochloric acid (HCl), more preferably with aqueous HCl solution; so as to obtain Compound (I). In an embodiment, HCl concentration in HCl solution ranges from 20 to 40% w/w, preferably from 25 to 35% w/w, more preferably HCl concentration is 30% w/w. In an embodiment, the initial molar ratio between Compound (II) and HCl ranges from 6 to 10, preferably from 7 to 9, more preferably the initial molar ratio between Compound (II) and HCl is 7.9. In an embodiment, reaction time of deprotection step (b) is at least 15 min, preferably at least 30 min. In an embodiment, reaction time of deprotection step (b) is not higher than 4 h, preferably not higher than 2 h, more preferably not higher than 1 h. In a preferred embodiment, reaction time ranges from 30 to 60 min. In an embodiment, deprotection step (b) is made in an aqueous solvent, preferably water. Advantageously, conversion of Compound (II) in Compound (I) after deprotection step (b) is at least 95%, preferably at least 98%, more preferably at least 99%.

According to an embodiment, deprotection step (b) is followed by a work-up and isolation step (b') comprising the following sub-steps:
(b'-1) extraction by a first polar aprotic organic solvent, preferably 2-methyltetrahydrofurane (2-MeTHF);
(b'-2) phase separation at a temperature ranging from 35 to 50° C., preferably from 40 to 45° C., and optionally washing by NaCl solution;
(b'-3) concentration and drying of organic phase;
(b'-4) solvent switch from the first solvent to a second polar aprotic organic solvent, preferably isopropyl acetate (iPAc);
(b'-5) recrystallisation by cooling; and
(b'-6) filtration, and optionally washing by methyl tert-butyl ether (MTBE); so as to obtain isolated Compound (I).

Advantageously, Compound (I) is obtained after work-up and isolation step (b') with at least 85% yield, preferably at least 90% yield, more preferably at least 95% yield. Advantageously, Compound (I) is obtained after work-up and isolation step (b') with at least 98% purity, preferably at least 99% purity, more preferably at least 99.9% purity.

Advantageously, no Compound (IV) salt of acid addition with hydrochloric acid (HCl) is formed during coupling step (a). Without being bound with any theory, the Applicant believes that protonation of Compound (IV) impacts negatively the conversion of coupling step (a).

The invention also relates to a novel process for manufacturing a compound of Formula (II) as previously described, preferably tert-butyl (1-(6-amino-2-isobutylpyrimidin-4-yl)azetidin-3-yl)(methyl)carbamate of Formula (II') as previously described. The compound of Formula (II) or (II') is manufactured by a process according to the invention as previously described, wherein deprotection step (b) is omitted, so as to obtain Compound (II) or (II').

A compound of Formula (III) as previously described can be manufactured by any suitable method of the art, known by a skilled artisan.

However, Compound (III) is preferably manufactured by a novel process according to the invention, comprising the following steps:
(i) synthesis of 6-amino-2-isobutylpyrimidin-4-ol (Compound (V), in short "(V)") by cycloaddition of 3-methylbutanimidamide acetate (or isobutylamidine acetate) (Compound (VI), in short "(VI)") with ethyl 2-cyanoacetate (Compound (VII), in short "(VII)"); and
(ii) synthesis of Compound (III) by chlorination of the hydroxyl group of Compound (V).

Synthesis of Compound (III) by the process of the invention is represented in Scheme 3 below:

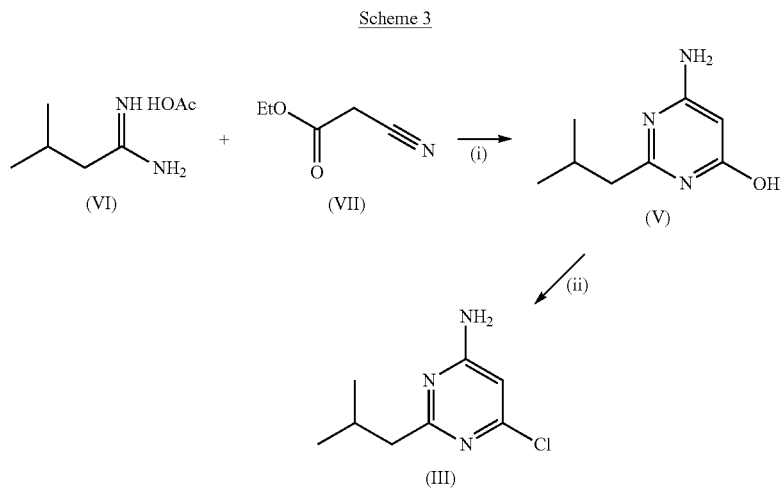

According to an embodiment, cycloaddition step (i) is performed in presence of a base, preferably a base being sodium ethoxide (NaOEt), in a solvent, preferably in ethanol (EtOH). In an embodiment, the temperature during cycloaddition step (i) ranges from 65 to 80° C., preferably from 70 to 75° C. In an embodiment, Compound (VII) is added to a solution comprising Compound (VI) and NaOEt. In an embodiment, the initial molar ratio at cycloaddition step (i) between Compound (VII) and Compound (VI) ranges from 1.0 to 1.25, preferably from 1.05 to 1.20, more preferably is 1.15. In an embodiment, the initial molar ratio at cycloaddition step (i) between NaOEt and Compound (VI) ranges from 1.25 to 1.75, preferably from 1.4 to 1.6, more preferably is 1.5.

In an embodiment, cycloaddition step (i) is followed by a work-up step (i') comprising a step of neutralization by acetic acid (AcOH). In an embodiment, cycloaddition step (i) or work-up step (i') is followed by an isolation step (i") comprising a step of filtration of Compound (V) out of water, and comprising optionally a step of washing Compound (V) with acetonitrile (ACN).

According to an embodiment, chlorination step (ii) is performed by means of phosphoryl chloride (POCl$_3$). In an embodiment, chlorination step (ii) is performed in a solvent, preferably in acetonitrile (ACN). In an embodiment, the temperature during chlorination step (ii) ranges from 60 to 90° C., preferably from 65 to 85° C., more preferably from 70 to 80° C. In an embodiment, the initial molar ratio at chlorination step (ii) between POCl$_3$ and Compound (V) ranges from 4 to 6, preferably from 4.5 to 5.5, more preferably is 5.

In an embodiment, chlorination step (ii) is followed by a quench step (ii') comprising the following sub-steps:
(ii'-1) concentration to minimal volume;
(ii'-2) successive stripping with a solvent, preferably toluene;
(ii'-3) quench of remaining phosphoryl chloride by addition of water;
(ii'-4) stirring of the mixture for at least 1 hour at a temperature ranging from 55 to 65° C., preferably 60° C.; and
(ii'-5) isolation of aqueous layer comprising Compound (III).

In an embodiment, chlorination step (ii) or quench step (ii') is followed by an isolation step (ii") comprising the following steps:

(ii"-1) addition of a solvent, preferably 2-methyltetrahydrofurane (2-MeTHF), preferably in 10 volumes;
(ii"-2) basification, preferably to pH 9;
(ii"-3) phase separation and solvent switch to a non-polar non-protic solvent, preferably n-heptane;
(ii"-4) filtration of Compound (III) and optional washing with a non-polar non-protic solvent, preferably n-heptane.

In a preferred embodiment, basification step (ii"-2) is made by means of ammonia (NH$_3$), preferably NH$_3$/H$_2$O solution with ammonia amount ranging from 25 to 30% w/w.

According to an embodiment, the process does not comprise any step of manufacture of a pinner salt from Compound (VII) before reaction with Compound (VI). A "Pinner salt" is a product of a Pinner reaction on a nitrile, i.e. a mineral acid salt of an imino ester. In an embodiment, the process does not comprise any step of manufacture of an intermediate compound from Compound (VII) before reaction with Compound (VI).

Compound (IV), and preferably Compound (IV'), can be manufactured by any suitable method of the art, known by a skilled artisan. For Example, Compound (IV') can be manufactured by the process represented on Scheme 4 below.

Scheme 4

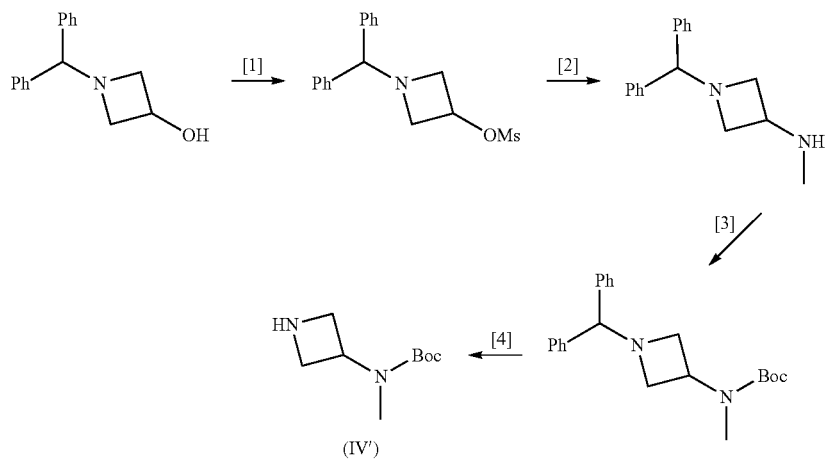

(IV')

This process comprising the following steps: [1] mesylation of 1-benzhydrylazetidin-3-ol; [2] amination of the resulting compound; [3] Boc-protection of the resulting compound; and [4] hydrogenation of the resulting compound so as to obtain Compound (IV').

An example of synthesis of Compound (IV') is disclosed in WO 2009/080721 patent application (Reference Example 2, page 72-73).

The invention also relates to a Compound of Formula (I) as previously described, the compound being manufactured by a process according to the invention.

The invention also relates to a Compound of Formula (II) as previously described, preferably a Compound of Formula (II') as previously described, the compound being manufactured by a process according to the invention.

Conversion can be monitored by any suitable method of the art, known by a skilled artisan. Preferably, conversion is measured by gas chromatography (GC) or high-performance liquid chromatography (HPLC). Purity of synthesized compounds can be determined by any suitable method of the art, known by a skilled artisan. Preferably, purity is determined by GC or by HPLC.

The present invention further relates to a composition comprising, consisting of or consisting essentially of at least one compound of Formula (I) or a pharmaceutically acceptable salt or solvate thereof.

The present invention further relates to a pharmaceutical composition comprising, consisting of or consisting essentially of at least one compound of Formula (I) or a pharmaceutically acceptable salt or solvate thereof and one or more pharmaceutically acceptable excipients.

The present invention further relates to a medicament comprising, consisting of or consisting essentially of at least one compound of Formula (I) or a pharmaceutically acceptable salt or solvate thereof.

As used herein, "consisting essentially of", with reference to a composition, pharmaceutical composition or medicament, means that the at least one compound of Formula (I) or pharmaceutically acceptable salt or solvate thereof is the only one therapeutic agent or agent with a biologic activity within said composition, pharmaceutical composition or medicament.

The compounds of Formula (I) of the invention may be in the form of pharmaceutically acceptable salts. Examples of pharmaceutically acceptable salts of the compounds of Formula I include, but are not limited to, the acid addition salts thereof. Suitable acid addition salts are formed from acids which form non-toxic salts. Examples of acid addition salts include the besylate, hydrochloride/chloride, malate, benzoate, ethane-1,2-disulfonate, fumarate, tartrate, acetate, adipate, ascorbate, aspartate, bicarbonate/carbonate, bisulphate/sulphate, borate, camsylate, citrate, cyclamate, edisylate, esylate, ethanesulfonate, formate, gluceptate, gluconate, glucuronate, glutamate, hexafluorophosphate, hibenzate, hydrobromide/bromide, hydroiodide/iodide, isethionate, lactate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, p-toluenesulfonate, tosylate, trifluoroacetate and xinofoate salts.

Examples of pharmaceutically acceptable excipients include, but are not limited to, water, saline, Ringer's solution, dextrose solution, and solutions of ethanol, starch, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, such as, for example, butylated hydroxyanisole (BHA), butylated hydroxytoluene (BHT), citric acid, ascorbic acid, tetracycline, and the like.

Carbopol® or "carbomer" refer to high molecular weight polymers of polyacrylic acid crosslinked with allyl sucrose or pentaerythritol allyl ether, said polymer comprising homopolymers and copolymers. Examples of Carbopol® include, but are not limited to, Carbopol® 910, Carbopol® 934, Carbopol® 940, Carbopol® 941, Carbopol® 974, Carbopol® 981, Carbopol® Ultrez and Polycarbophil.

Other examples of pharmaceutically acceptable excipients that may be used in the composition of the invention include, but are not limited to, ion exchangers, alumina, magnesium stearate, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In addition, pharmaceutically acceptable excipients may also comprise, without limitation, surfactants (e.g., hydroxypropylcellulose); suitable carriers, such as, for example, solvents and dispersion media containing, for example, water, ethanol, polyol (e.g., glycerol, propylene glycol, and liquid polyethylene glycol, and the like), suitable mixtures thereof, and vegetable oils, such as, for example, peanut oil and sesame oil; isotonic agents, such as, for example, sugars or sodium chloride; coating agents, such as, for example, hydroxypropylmethylcellulose (HPMC), polyethylene glycol (PEG), polysorbate 80, titanium dioxide and lecithin; agents delaying absorption, such as, for example, aluminum monostearate and gelatin; preservatives, such as, for example, benzalkonium chloride, benzethonium chloride, chlorobutanol, thimerosal and the like; buffers, such as, for example, boric acid, sodium and potassium bicarbonate, sodium and potassium borates, sodium and potassium carbonate, sodium acetate, sodium biphosphate and the like; tonicity agents, such as, for example, dextrose, potassium chloride, propylene glycol, sodium chloride; antioxidants and stabilizers, such as, for example, sodium bisulfite, sodium metabisulfite, sodium thiosulfite, thiourea and the like; nonionic wetting or clarifying agents, such as, for example, polysorbate 80, polysorbate 20, poloxamer 282 and tyloxapol; viscosity modifying agents, such as, for example dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose; diluents, adjuvants and the like.

The present invention further relates to a compound of Formula (I) for treating (or for use in the treatment of) a disease mediated by the H4 histamine receptor.

Another object of the present invention relates to a method of treating a disease mediated by the histamine H4 receptor in a subject in need thereof, preferably in a human subject, which comprises administering to said subject at least one compound of Formula (I) or a pharmaceutically acceptable salt or solvate thereof.

In one embodiment, the method of the invention is for preventing a disease mediated by the histamine H4 receptor. In another embodiment, the method of the invention is for alleviating at least one symptom of a disease mediated by the histamine H4 receptor or for curing a disease mediated by the histamine H4 receptor.

In one embodiment, a therapeutically effective amount of the at least one compound of Formula (I) is administered or is to be administered to the subject.

Another object of the present invention is the use of a compound of Formula (I) or a pharmaceutically acceptable salt thereof for the manufacture of a medicament for the treatment of a disease mediated by the H4 histamine receptor.

In one embodiment, said disease mediated by the H4 histamine receptor is an allergic, immunological or inflammatory disease or pain.

Examples of allergic, immunological or inflammatory diseases include, but are not limited to, respiratory diseases, ocular diseases, skin diseases, inflammatory bowel diseases, diabetes, rheumatoid arthritis, multiple sclerosis, cutaneous lupus, systemic lupus erythematosus and transplant rejection.

In one embodiment, the allergic, immunological or inflammatory disease is selected from the group comprising asthma, allergic rhinitis, chronic obstructive pulmonary disease (COPD), allergic rhinoconjunctivitis, dry eye, cataracts, dermatitis (e.g., atopic dermatitis), psoriasis, urticaria, pruritus, ulcerative colitis, Crohn's disease, diabetic nephropathy, rheumatoid arthritis, multiple sclerosis, cutaneous lupus, systemic lupus erythematosus and transplant rejection.

Examples of pains include, but are not limited to, inflammatory pain, inflammatory hyperalgesia, hyperalgesia, post-surgical pain, migraine, cancer pain, visceral pain, osteoarthritis pain and neuropathic pain.

In one embodiment, the disease mediated by the H4 histamine receptor is an ear disorder.

In one embodiment, the disease mediated by the H4 histamine receptor is a vestibular disorder. In one embodiment, said vestibular disorder is a lesional vestibular disorder. In another embodiment, said vestibular disorder is a non-lesional vestibular disorder.

Examples of vestibular disorders include without limitation, vestibular migraine, vestibular neuritis (including, without limitation, vestibular neuronitis, viral neuronitis, labyrinthitis, viral endolymphatic labyrinthitis, serous labyrinthitis, suppurative labyrinthitis), acute unilateral vestibulopathy, vertigo and dizziness (including, without limitation, migraine-associated vertigo, spontaneous episodic vertigo, benign positional paroxysmal vertigo, familial episodic vertigo, age-related dizziness and imbalance, motion sickness, mal de debarquement), vestibular ototoxicity (including, without limitation, compound-induced and drug-induced ototoxicity, i.e., inducing impairment of the vestibule function leading to vestibular deficits, and induced by compounds listed without limitation above), vestibule-toxic impairments, hydrops (including, without limitation, endolymphatic hydrops, secondary endolymphatic hydrops), Ménière's disease (including, without limitation, spell of Ménière's disease, chronic Ménière disease), fistula (including, without limitation, perilymphatic fistula, labyrinthine fistula), trauma (including, without limitation, head trauma with labyrinthine haemorrhage, barotrauma), infections (including, without limitation, chronic or acute labyrinthine infection), autoimmune inner ear disease, benign or malignant tumors (including, without limitation, vestibular schwannomas, acoustic neuroma), presbyvestibula, vestibular syndromes after chirurgical treatments of middle ear, channelopathies, superior semicircular canal dehiscence, endolymphatic sac or pontocerebellar angle, ataxia (including, without limitation, episodic ataxia), enlarged vestibular aqueduct, bilateral vestibular hypofunction, neurotoxic vestibulopathy, pediatric vestibular disorder, Cogan syndrome, vestibular hyperacusis, vertebrobasilar insufficiency.

Examples of lesional vestibular disorders include, without limitation, vestibular migraine, vestibular neuritis (including, without limitation, vestibular neuronitis, viral neuronitis, labyrinthitis, viral endolymphatic labyrinthitis, serous labyrinthitis, suppurative labyrinthitis), acute unilateral vestibulopathy, vertigo and dizziness (including, without limitation, migraine-associated vertigo, spontaneous episodic vertigo, familial episodic vertigo, age-related dizziness and imbalance), vestibular ototoxicity (including, without limitation, compound-induced and drug-induced ototoxicity, i.e., inducing impairment of the vestibule function leading to vestibular deficits, and induced by compounds listed without limitation above), vestibule-toxic impairments, hydrops (including, without limitation, endolymphatic hydrops, secondary endolymphatic hydrops), Ménière's disease (including, without limitation, spell of Ménière's disease, chronic Ménière disease), fistula (including, without limitation, perilymphatic fistula, labyrinthine fistula), trauma (including, without limitation, head trauma with labyrinthine haemorrhage, barotrauma), infections (including, without limitation, chronic or acute labyrinthine infection), autoimmune inner ear disease, benign or malignant tumors (including, without limitation, vestibular schwannomas, acoustic neuroma), presbyvestibula, vestibular syndromes after chirurgical treatments of middle ear, channelopathies, superior semicircular canal dehiscence, endolymphatic sac or pontocerebellar angle, ataxia (including, without limitation, episodic ataxia), enlarged vestibular aqueduct, bilateral vestibular hypofunction, neurotoxic vestibulopathy, pediatric vestibular disorder, Cogan syndrome, vestibular hyperacusis, vertebrobasilar insufficiency.

Examples of non-lesional vestibular disorders include, without limitation, benign positional paroxysmal vertigo, motion sickness and mal de debarquement.

Another object of the invention is a method for restoring vestibular functionality in a subject in need thereof, preferably in a subject affected with a vestibular disease, more preferably with a lesional vestibular disease, comprising or consisting of administering to the subject a therapeutically effective amount of at least one compound of Formula (I) or a pharmaceutically acceptable salt or solvate thereof.

In one embodiment, the method of the invention is for preventing a vestibular disorder, preferably a lesional vestibular disease. In another embodiment, the method of the invention is for alleviating a symptom of a vestibular disorder, preferably a lesional vestibular disease or for curing a vestibular disorder, preferably a lesional vestibular disease.

In one embodiment, the disease mediated by the H4 histamine receptor is tinnitus.

In one embodiment, the disease mediated by the H4 histamine receptor is hearing loss.

In one embodiment, the disease mediated by the H4 histamine receptor is vertigo or dizziness. In one embodiment, the disease mediated by the H4 histamine receptor is selected from the group comprising migraine-associated vertigo, spontaneous episodic vertigo, familial episodic vertigo, age-related dizziness and imbalance.

In one embodiment, the compound, composition, pharmaceutical composition or medicament of the invention is to be administered systemically or locally.

In one embodiment, the compound, composition, pharmaceutical composition or medicament of the invention is to be administered by injection, orally, topically, nasally, by inhalation, buccally, rectally, intratracheally, transmucosally, transtympanically, by percutaneous administration, intramuscularly or by parenteral administration.

In one embodiment, the compound, composition, pharmaceutical composition or medicament of the invention is to be administered by injection, preferably is to be systemically injected. Examples of formulations adapted to systemic injections include, but are not limited to, liquid solutions or suspensions, solid forms suitable for solution in, or suspension in, liquid prior to injection. Examples of systemic injections include, but are not limited to, intravenous, subcutaneous, intramuscular, intradermal, intravitreal, and intraperitoneal injection, or perfusion. In another embodiment, when injected, the compound, composition, pharmaceutical composition or medicament of the invention is sterile. Methods for obtaining a sterile pharmaceutical composition include, without limitation, sterile filtration, terminal sterilization (dry heat, radiation, moist heat, gases, gamma radiation) or sterilization via aseptic processing.

In one embodiment, the compound, composition, pharmaceutical composition or medicament of the invention is to be systemically administered, preferably is to be orally administered. Examples of formulations adapted to oral administration include, but are not limited to: solid forms, liquid forms and gels. Examples of solid forms adapted to oral administration include, but are not limited to, pill, tablet, capsule, soft gelatine capsule, hard gelatine capsule, caplet, compressed tablet, cachet, wafer, sugar-coated pill, sugar coated tablet, or dispersing and/or disintegrating tablet, powder, solid forms suitable for solution in, or suspension in, liquid prior to oral administration and effervescent tablet. Examples of liquid forms adapted to oral administration include, but are not limited to, solutions, suspensions, drinkable solutions, elixirs, sealed phial, potion, drench, syrup and liquor.

In another embodiment, the compound, composition, pharmaceutical composition or medicament of the invention is to be topically administered. Examples of formulations adapted to topical administration include, but are not limited to, sticks, waxes, creams, lotions, ointments, balms, gels, masks, leave-on washes and/or the like.

In one embodiment, the compound, composition, pharmaceutical composition or medicament of the invention is to be administered directly in the ear, in particular, in the inner ear, in the middle ear, in the external ear, in the cochlea, or in the vestibule by transtympanic or intratympanic administration. This administration route may be preferred for introducing a direct and long term effect on the ear. Said administration can be accomplished topically or by injection. Delivery techniques for such administration may include the use of devices or drug carriers to transport and/or deliver the active principle to the ear, where it diffuses into the ear, is actively infused or is injected. Examples of formulations adapted to such administration include, but are not limited to, otowicks, round window catheters, various types of gels, foams, fibrins, emulsions, solutions, patches or other drug carriers, which are placed in the ear, and loaded with the composition of the invention for sustained release. It may also include devices that are inserted into the cochlear duct or any other part of the cochlea.

The diffusion of the composition across middle-inner ear interface tissue structures, in particular the round window membrane, depends on a variety of factors, such as molecular weight, concentration, liposolubility, electrical charge, and thickness of the membrane.

In one embodiment, the compound of Formula (I) is to be administered in an immediate-release form.

In one embodiment, the compound of Formula (I) is to be administered in a sustained-release form. In one embodiment, the composition, the pharmaceutical composition or the medicament of the invention thus comprises a delivery system that controls the release of the at least one compound of Formula I or of a salt or solvate thereof.

In one embodiment, the compound of Formula (I) is formulated as a depot formulation, i.e., as a long acting parenteral (e.g., injectable) formulation designed to provide slow, sustained and prolonged action. Depot formulations may be placed subcutaneously or intramuscularly, for example. The release of the compound of Formula (I) may either be pulsatile or continuous depending on the structure of the device and the polymer characteristics. Depot formulations may be in the form of microparticles, implants (e.g., rod-shaped), or solid boluses that form in situ. Most depot formulations comprise biodegradable polymer excipients.

The polymer excipient controls the rate of drug release and resorbs during and/or after drug release. Examples of biodegradable polymers include, but are not limited to, lactide/glycolide polymers. These resorbable polymers are biocompatible and have a long safety record in humans. They resorb solely by hydrolysis, initially to lactic acid and glycolic acid, and eventually to carbon dioxide and water.

It will be understood that the total daily usage of the compound of Formula (I) or a pharmaceutically acceptable salt or solvate thereof; or of the composition, pharmaceutical composition or medicament comprising thereof will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific composition employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the compound of Formula (I) or a pharmaceutically acceptable salt or solvate thereof may be varied over a wide range from about 0.1 to about 10000 mg per adult per day, preferably 0.1 to about 2000, more preferably from about 0.1 to about 500 mg per adult per day, more preferably from about 1 to about 200 or 300 mg per adult per day.

EXAMPLES

The present invention is further illustrated by the following examples.

Materials and Methods

Material tert-butyl azetidin-3-yl(methyl)carbamate of Formula (IV') [Compound (IV')] was prepared according to literature methods. 3-Methylbutanimidamide acetate [Compound (VI)], ethyl 2-cyanoacetate [Compound (VII)], and all others reactants and solvents were purchased from commercial sources and used without further purification.

Methods

Conversion was measured by GC or by HPLC. Purity of synthesized compounds was determined by GC.

Example 1: Synthesis of Compound (V) [6-amino-2-isobutylpyrimidin-4-ol]

Reaction: 3-Methylbutanimidamide acetate [Compound (VI)] (20.0 g; 125 mmol; 1.0 eq) was suspended in EtOH (40 ml; 2 rel vols). NaOEt 21 wt-% (60.7 g; 187 mmol; 1.5 eq.) was charged and heated to 70° C. A solution of ethyl 2-cyanoacetate [Compound (VII)] (16.2 g; 144 mmol; 1.15 eq.) in EtOH (20 ml; 2 vols) is dosed slowly (about 4 hours). Conversion was checked by GC after 40% addition [Compound (V) 45%] and 100% addition [Compound (V) 69%]. Conversion was checked by GC after reaction for 21 hours at 70° C. [85% Compound (V)]. The mixture was stirred overnight at 70° C.

Work-up and isolation: Mixture was cooled to 50° C. then quenched with AcOH (0.55 eq.; 4.13 g). Water (8 vols) was charged. Mixture is concentrated at 50-55° C. to about 7 vols. Suspension stripped with ACN (3 vols) to a final volume of about 6 vols, then cooled to 0-5° C. Mixture was further diluted with water (2 vols) and stirred for 2 hours. Solids were filtered off, washed with water/ACN 1/1 (3 vols), ACN (2 vols) and dried under nitrogen flow for 1 hour.

Results: 6-Amino-2-isobutylpyrimidin-4-ol [Compound (V)] was isolated in good yield (17.9 g, 86%) and in high purity (100%).

Example 2: Synthesis of Compound (III) [6-chloro-2-isobutylpyrimidin-4-amine]

Reaction: 6-amino-2-isobutylpyrimidin-4-ol [Compound (V)] (30.0 g; 179 mmol; 1.0 eq) from Example 1 was suspended in ACN (150 ml; 5 vols) at room temperature (RT). $POCl_3$ (138 g; 897 mmol; 5.0 eq.) was charged. The suspension was heated step wise to 60° C., 65° C. then 70° C. and stirred at 70° C. for 15 minutes. The suspension was further heated to 80° C. and stirred overnight. Conversion was checked with HPLC after 19 hours at 80° C. ([Compound (III)] 98.9%).

Work-up: The mixture was concentrated at 60-70° C. to about 3 rel vols. The mixture was stripped 3 times with toluene (3 vols) at 60-70° C., diluted with toluene (2 vols) then temperature was adjusted to ±50° C. The mixture was quenched with water (5 vols). Temperature was adjusted to 60° C. and the mixture was stirred for at least 30 minutes at 55-65° C. Phase separation: AL was isolated and transferred back to the reactor and diluted with water (1 vol). Temperature was adjusted to 20-25° C.

Isolation: 2-MeTHF (10 vols) was charged. Dose controlled adjusted the pH to 9-10 with $NH_3/H_2O$ 25-30% (about 2.5 vols). Phase separation: AL was drummed off and discarded; oil layer (OL) was kept in the reactor. OL was washed with water (2 vols) and concentrated at 40-50° C. to 4 rel vols. OL was stripped 2 times with n-heptane (3 vols) at 40-50° C. Suspension was cooled to 0-5° C. and stirred for 1 hour. Solids were filtered off, washed twice with n-heptane (2 vols) and dried under nitrogen flow.

Results: 6-Chloro-2-isobutylpyrimidin-4-amine [Compound (III)] was isolated in good yield (29.2 g, 88%) and in high purity (99.8%).

Example 3: Synthesis of Compound (II') [tert-butyl (1-(6-amino-2-isobutylpyrimidin-4-yl)azetidin-3-yl)(methyl)carbamate]

Reaction: 6-chloro-2-isobutylpyrimidin-4-amine [Compound (III)] (25.0 g; 135 mmol; 1.0 eq) from Example 2 and $K_2CO_3$ (22.3 g; 162 mmol; 1.2 eq.) were charged to the reactor. Tert-butyl azetidin-3-yl(methyl)carbamate [Compound (IV')] (26.1 g, 140 mmol, 1.04 eq.) dissolved in DMSO ($m_{solution}$=148 g, 17.6 wt-%) was charged and the mixture was heated to 110° C. Conversion was measured after 24 hours (Compound (II') 93%).

Work-up and isolation: The mixture was cooled to 50-60° C. then was diluted with water (6 vol) and EtOAc (10 vol) and stirred for 5 min. Phase separation: the OL was isolated then washed with water (2 vol). The OL was concentrated to about 6 rel. vols. at 65-75° C. The solution was stripped 3 times with iPAc (4 vol). The solution was cooled slowly to RT. The suspension was cooled further to 0-5° C. After 30 min of stirring, the solids were filtered off, washed twice with MTBE (2 vols) and dried under nitrogen purge.

Purification: The isolated product was suspended in iPAc (100 ml, 4 vol) and heated until dissolution. The mixture was cooled to RT. The suspension was further cooled to 0-5° C.

After 1 hour of stirring, the solids were filtered off, washed twice with MTBE (2 vols) and dried under nitrogen purge.

Results: Tert-butyl (1-(6-amino-2-isobutylpyrimidin-4-yl)azetidine-3-yl)(methyl)carbamate [Compound (II')] was obtained in high yield (40.6 g, 89.9%) and in high purity (99.8%) after "work-up and isolation" step as described hereabove. Compound (II') was isolated in high yield (38.7 g, 85.6%) and in high purity (99.9%) after further "Purification" step as described hereabove.

Example 4: Synthesis of Compound (I) [2-isobutyl-6-(3-(methylamino)azetidin-1-yl)pyrimidin-4-amine]

Reaction: tert-butyl (1-(6-amino-2-isobutylpyrimidin-4-yl)azetidine-3-yl)(methyl)carbamate [Compound (II)] (20.0 g; 59.6 mmol; 1.0 eq) from Example 3 was suspended in water (50 ml; 2.5 vols) at RT. HCl 30% (50 ml; 470 mmol; 7.9 eq.) was dosed over 15 min below 30° C. Mixture was stirred at 25-30° C. Conversion was measured with HPLC after 30 min at 25-30° C. (Compound (I) 99.1%).

Work-up and isolation: Reaction mixture was cooled to 20° C. 2-MeTHF (15 vols) was charged. pH was adjusted to 11-12 with an aqueous NaOH solution (33%, about 63 g). Temperature was allowed to go up to 40° C. Phase separation at 40-45° C.: AL was drummed off and discarded; OL was kept in the reactor. OL was washed with a NaCl solution (20%, 1 vol) at 40° C. OL was concentrated to about 10 vols and dried with Dean-Stark apparatus. A screening filtration was performed and the reactor was cleaned. OL was concentrated at 60-65° C. to about 5 vols. The solution was stripped atmospherically 3 times with iPAc (3 vol), $T_{end}$=88-89° C. Suspension was cooled slowly until crystallization. Solids were filtered off, washed twice with MTBE (2 vols) and dried.

Results: 2-Isobutyl-6-(3-(methylamino)azetidin-1-yl)pyrimidin-4-amine [Compound (I)] was isolated in high yield (13.2 g, 94%) and in high purity (99.9%).

The invention claimed is:
1. A process for manufacturing 2-isobutyl-6-(3-(methylamino)azetidin-1-yl)pyrimidin-4-amine of Formula (I):

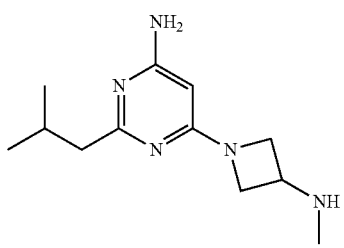

Formula (I)

said process comprising the following steps:
(a) reacting 6-chloro-2-isobutylpyrimidin-4-amine of Formula (III):

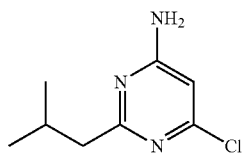

Formula (III)

with a N-protected N-methylazetidin-3-amine of Formula (IV):

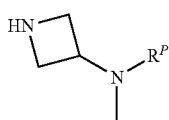

Formula (IV)

wherein $R^P$ is a protecting group selected from Carbobenzyloxy (Cbz), p-Methoxybenzyl carbonyl (Moz), tert-Butyloxycarbonyl (Boc), 9-Fluorenylmethyloxycarbonyl (Fmoc), Acetyl (Ac), Benzoyl (Bz), Benzyl (Bn), Carbamate, p-Methoxybenzyl (PMB), 3,4-Dimethoxybenzyl (DMPM), p-Methoxyphenyl (PMP), Tosyl (Ts), and Trichloroethyl chloroformate (Troc);
in an organic solvent, wherein said organic solvent is dimethylsulfoxide;
in the presence of a base, wherein said base is potassium carbonate;
at a temperature ranging from 85 to 125° C.;
the initial molar ratio between said compound of Formula (IV) and said compound of Formula (III) ranging from 0.85 to 1.25;
so as to obtain an intermediate protected compound of Formula (II):

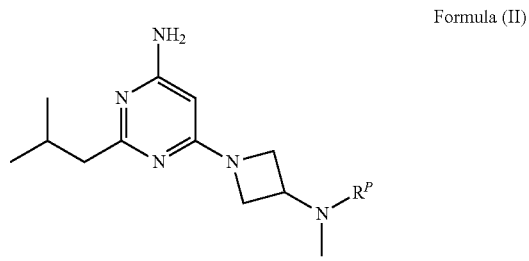

Formula (II)

and
(b) performing a N-deprotection of said compound of Formula (II);
so as to obtain said compound of Formula (I).

2. The process according to claim 1, wherein protecting group $R^P$ is tert-Butyloxycarbonyl (Boc) or Tosyl (Ts).

3. The process according to claim 1, wherein protecting group $R^P$ is tert-Butyloxycarbonyl (Boc).

4. The process according to claim 1, wherein the initial molar ratio at coupling step (a) between said compound of Formula (IV) and said compound of Formula (III) ranges from 0.90 to 1.20.

5. The process according to claim 4, wherein the initial molar ratio at coupling step (a) between said compound of Formula (IV) and said compound of Formula (III) ranges from 0.95 to 1.10.

6. The process according to claim 5, wherein the initial molar ratio at coupling step (a) between said compound of Formula (IV) and said compound of Formula (III) is 1.04.

7. The process according to claim 1, wherein the temperature during coupling step (a) ranges from 90 to 120° C.

8. The process according to claim 7, wherein the temperature during coupling step (a) ranges from 100 to 120° C.

9. The process according to claim 8, wherein the temperature during coupling step (a) is 110° C.

10. The process according to claim 1, wherein the reaction time of coupling step (a) ranges from 16 h to 32 h.

11. The process according to claim 1, wherein coupling step (a) is followed by a workup and isolation step (a') comprising the following steps:
(a'-1) dilution of reaction mixture with water and with a first polar aprotic organic solvent;
(a'-2) phase separation, and optionally washing by water;
(a'-3) solvent switch from the first solvent to a second polar aprotic organic solvent;
(a'-4) recrystallisation by cooling; and
(a'-5) filtration;
to afford said compound of Formula (II).

12. The process according to claim 11, wherein said polar aprotic organic solvent at dilution step (a'-1) is ethyl acetate.

13. The process according to claim 11, wherein said polar aprotic organic solvent at solvent switch step (a'-3) is isopropyl acetate.

14. The process according to claim 1, wherein coupling step (a) or workup and isolation step (a') is followed by a purification step (a'') comprising a step of recrystallisation of said compound of Formula (II) in a polar aprotic organic solvent.

15. The process according to claim 1, wherein deprotection step (b) is made by means of contacting said compound of Formula (II) with dilute aqueous hydrochloric acid solution.

16. The process according to claim 15, wherein the initial molar ratio between said compound of Formula (II) and hydrochloric acid ranges from 6 to 10.

17. A process for manufacturing a compound of Formula (II):

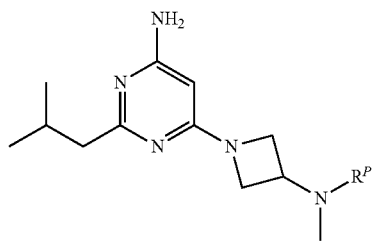

Formula (II)

wherein $R^P$ is a protecting group selected from Carbobenzyloxy (Cbz), p-Methoxybenzyl carbonyl(Moz), tert-Butyloxycarbonyl (Boc), 9-Fluorenylmethyloxycarbonyl (Fmoc), Acetyl (Ac), Benzoyl (Bz), Benzyl (Bn), Carbamate, p-Methoxybenzyl (PMB), 3,4-Dimethoxybenzyl (DMPM), p-Methoxyphenyl (PMP), Tosyl (Ts) and Trichloroethyl chloroformate (Troc);
said process comprising reacting 6-chloro-2-isobutylpyrimidin-4-amine of Formula (III):

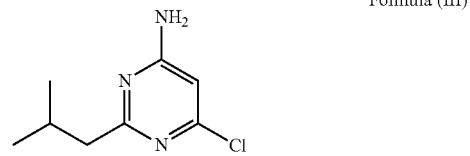

Formula (III)

with a N-protected N-methylazetidin-3-amine of Formula (IV):

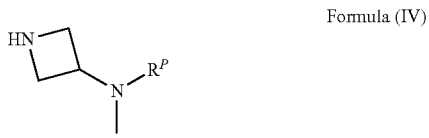

Formula (IV)

in an organic solvent, wherein said organic solvent is dimethylsulfoxide;
in the presence of a base, wherein said base is potassium carbonate;
at a temperature ranging from 85 to 125° C.;
the initial molar ratio between said compound of Formula (IV) and said compound of Formula (III) ranging from 0.85 to 1.25;
so as to obtain said compound of Formula (II).

18. The process according to claim 5, wherein the initial molar ratio at coupling step (a) between said compound of Formula (IV) and said compound of Formula (III) ranges from 0.99 to 1.09.

19. The process according to claim 8, wherein the temperature during coupling step (a) ranges from 105 to 115° C.

20. The process according to claim 10, wherein the reaction time of coupling step (a) ranges from 20 to 24 h.

21. The process according to claim 14, wherein said polar aprotic organic solvent is isopropyl acetate.

* * * * *